(12) United States Patent
Sohn

(10) Patent No.: US 6,565,536 B1
(45) Date of Patent: May 20, 2003

(54) SYSTEM FOR CATHETER FIXATION

(75) Inventor: Ze'ev Sohn, Modiin (IL)

(73) Assignee: SRS Medical Systems, Inc., North Billerica, MA (US)

( * ) Notice: Subject to any disclaimer, the term of this patent is extended or adjusted under 35 U.S.C. 154(b) by 0 days.

(21) Appl. No.: 09/412,151

(22) Filed: Oct. 5, 1999

Related U.S. Application Data

(63) Continuation of application No. 08/571,210, filed on Dec. 12, 1995, now abandoned.

(30) Foreign Application Priority Data

Dec. 12, 1994 (IL) .................................................. 111953

(51) Int. Cl.⁷ ................................................ A61M 5/32
(52) U.S. Cl. ................................ 604/174; 128/DIG. 26
(58) Field of Search .................................. 604/174, 175, 604/177, 178, 179, 180, 104–107; 128/DIG. 26

(56) References Cited

U.S. PATENT DOCUMENTS 3,397,699 A * 8/1968 Kohl ............................ 604/105
5,232,451 A * 8/1993 Freitas et al.

* cited by examiner

Primary Examiner—Sharon Kennedy
Assistant Examiner—Michael M Thompson
(74) Attorney, Agent, or Firm—Cesari and McKenna, LLP

(57) ABSTRACT

A catheter device for fixation to the human body comprises a catheter having a distal end and a proximal end, the distal end comprising one or more fins, the fins having an open position defining a large diameter and a closed position of small diameter. The catheter has a catheter body and a push tube sliding axially within the catheter body for manipulating the fins into the open and closed positions.

3 Claims, 5 Drawing Sheets

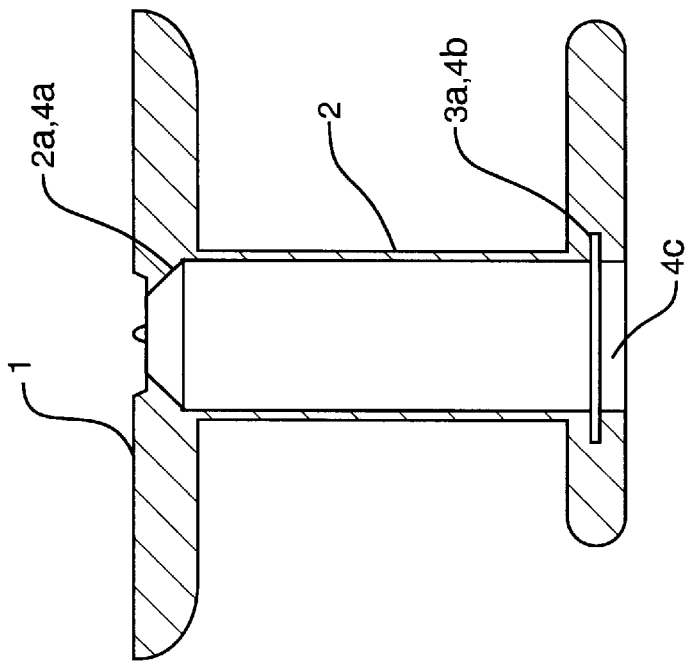
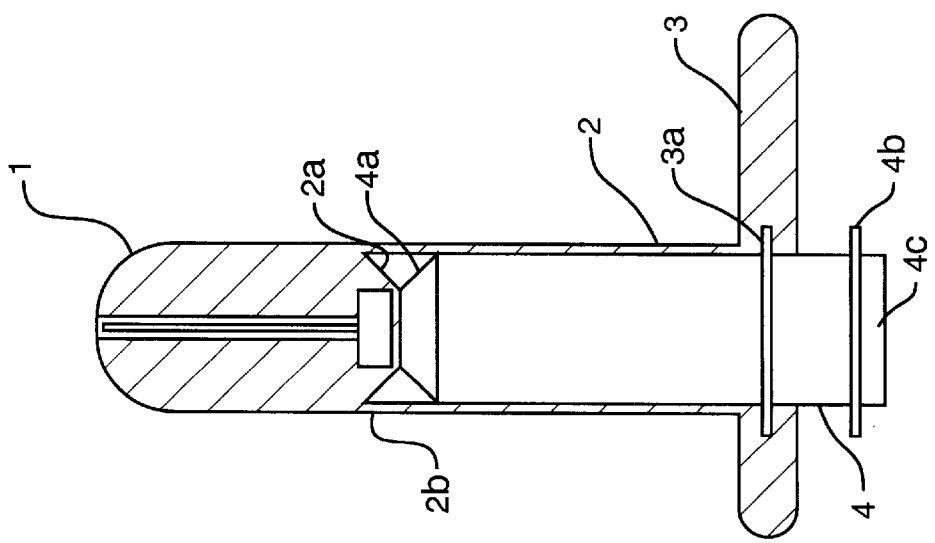

SYSTEM FOR CATHETER FIXATION

RELATED APPLICATIONS

This application is a continuation of U.S. patent application Ser. No. 08/571,210 filed Dec. 12, 1995 abandoned, which claims priority under 35 U.S.C. §119 to Israeli Patent Application No. 111953 filed Dec. 12, 1994. This application claims the priority of both prior applications, the disclosures of which are fully incorporated herein by reference.

BACKGROUND OF THE INVENTION

Body cavities are drained or fed with different types of tubes. Examples of such cavities include the urinary bladder cavity, the gastric or intestinal cavity and the post-operative cavity. Also, cystic ducts and gall bladder spaces and other such cavities are drained or fed with rigid or flexible tubes. The flexible tubes are made of biocompatible polymer materials such as silicone, polyethylene, etc. These tubes have an external part (out of the body or the organ) and an internal part. The external part of these tubes are exposed to accidental pulling forces which may cause the tube to dislodge out of the body.

Different methods of tube fixation to the body exist. External fixation (skin contact fixation) of the tube includes: fastening the tube to the skin with adhesive tapes and/or suturing the tube to the skin with surgical threads.

Internal fixation methods include:

balloon inflation of the tube tip to enlarge its diameter and increase its pull-out force resistance;

use of a catheter tip which flares outward to a large diameter by flexing of the catheter wall. Examples of such devices are known as Malleot or Petzer catheters. In those systems, fins which are normally flared open form the enlarged tip of the catheter. A constant force is required to press the flares concentrically to insert or remove the catheter.

The main advantage of the present balloon fixation system over the Malleot and Petzer catheters is the fact that the balloon catheter is inserted and removed in substantially the same low profile diameter whereas with the Malleot and Petzer catheters a substantial pull-out force is required to close the flare and enable catheter removal. During pull-out of the prior art catheters, the flares apply a radial and shearing force on the body tissue surrounding the tube which may cause unnecessary pain and trauma.

Another disadvantage of the Malleot and Petzer flared catheter fixation systems is the low fixation force of the tube within the body. This fixation force is limited because of the resulting desirably small pull-out force to remove the tube. This pull-out force, as mentioned, may cause trauma to the tissue.

The main disadvantage of the balloon fixation method is its relatively complicated insertion procedure requiring the need for a syringe to inflate the balloon. Also, the balloon's large area of contact with the body tissue can cause substantial tissue irritability.

A means for remotely opening and closing flares in the body will allow for easy insertion and removal of a catheter with a flare-type fixation system. Also, remotely closing the flares, before removing the catheter, allow flares with high fixation forces to be used without causing any trauma to the tissue during removal.

SUMMARY OF THE INVENTION

The invention relates to a system for catheter fixation to a body by enlarging or reducing a catheter tip diameter during insertion to or removal from the body. More particularly, the invention also relates to a medical grade flexible polymer tube which is used mainly as a drainage tube but is not limited to drainage systems. It may also be used for urological intra-urethral sphincters, plugs or devices or may be used as urethral, ureteral, bronchial or esophageal catheters.

In another embodiment of the invention, the system is used for closing body organ holes such as atrio-ventricular septal defects, arterial punctures, gastric or intestinal leakage from a fistula, or any passage or hole to be obstructed.

The invention enables the enlargement (and reduction) of the catheter tip diameter when located in the body by an external manipulation thereby fixing the catheter in place. Another manipulation, external to the body or organ, is used to return the tip diameter to its original small diameter size prior to catheter removal.

The invention also relates to a catheter, tube or plug with a distal-end tip that is made up of one or more fins which can flare outwardly thereby increasing the diameter of the catheter tip and holding the catheter in position in the body.

The invention also relates to a push-tube which is used to force the fins to flare open.

The invention also relates to a system which selectively locks the fins in the stressed or flared-open position.

The invention also relates to equipment which aids in the installation of a catheter in the human body and its removal from the body.

All these embodiments will become clear in the detailed description of the invention and the attached figures.

BRIEF DESCRIPTION OF THE DRAWINGS

FIG. 2 is a cross section of the uretheral catheter or plug in its closed and open positions;

DETAILED DESCRIPTION OF THE DRAWINGS AND THE PREFERRED EMBODIMENT

Figure 1B:
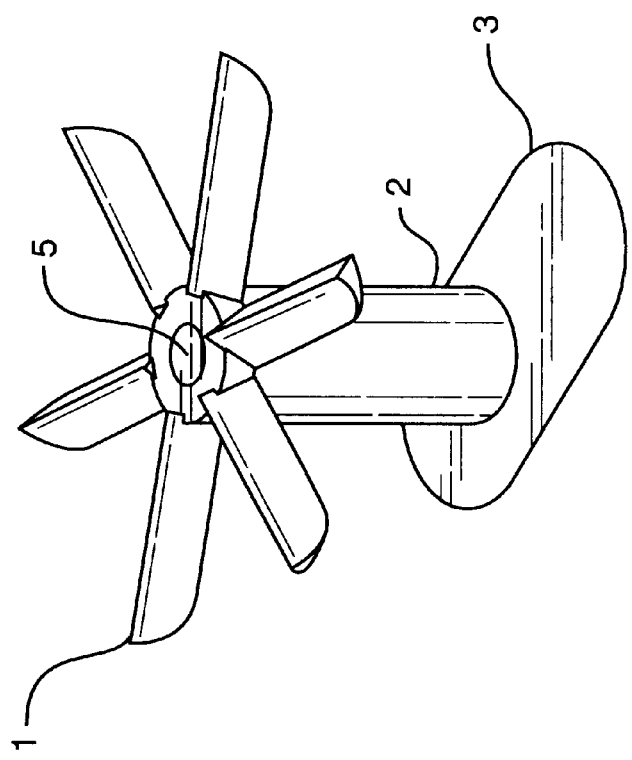
FIG. 1 is a perspective view of a urethral catheter or plug in its closed and open positions.
Figure 1A:
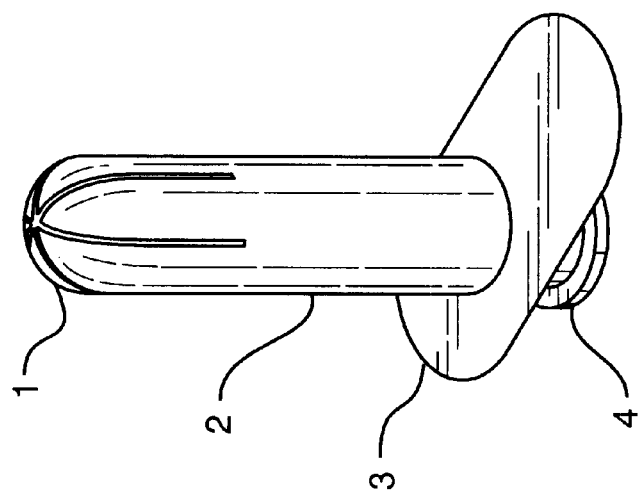

The invention is herein described by way of example with reference to the accompanying drawings, wherein:

FIG. 1 shows one embodiment of this invention. In this embodiment the catheter is designed for insertion in the female urethra. The catheter is shown with the fins in the open and closed positions. The fins open within the bladder and prevent the catheter from sliding out of the body. Element 1 designates the fins. Element 2 refers to the catheter body. Element 3 designates the part of the catheter used to lock the fins in an open or closed position. Element 3 has an enlarged cross section which remains external to the urethra and prevents the catheter from sliding into the bladder. Element 4 designates a push-tube used to remotely open and close the fins. Element 5 designates a lumen extending through the catheter. FIG. 2 shows a cross-section of this catheter in its open and closed positions.

As shown in FIG. 2, at one end, the push-tube has an angled tip designated 4a. The catheter body also has an angled portion (designated 2a) which opposes element 4a. In the closed position, elements 4a and 2a do not have the same angle. If the push tube is pushed into the catheter body then element 4a begins to push against element 2a. The fin material and shape are designed so that the base of the fin is flexible enough to allow rotation of the fin around the horizontal pivot lines. The force from the push-tube against the surface 2a forces the fins to begin rotating outward about pivot lines 2b. When surface 2a rotates until it fully contacts surface 4a, then the fins are in the fully open position. This is shown in the left side of FIG. 2. These fins hold a catheter in position in the human body.

One part of the push-tube, designated 4b, has a different diameter than the rest of the tube. The catheter body also has a section with a different diameter (designated 3a) which mates with 4b. The push-tube can slide freely in and out of the catheter body until element 4b mates with element 3a. In order for element 4b to mate with element 3a, one or both of these must first be deformed. After surface 4b mates with 3a, the push-tube no longer can slide relative to the catheter body and is locked in position. As shown in the open embodiment in FIG. 2, locking the push-tube in position in the catheter body locks the fins in the open position.

If element 3 is deformed so that 4b can slide out of 3a, then the push-tube can slide out of the catheter body. Furthermore, the elastic properties of the catheter tend to pull the fins back to their normally closed position. This elastic force also helps to push the tube out of the catheter body. Consequently, once 4b is released from 3a, the catheter returns automatically to its normally closed arrangement, illustrated in the right side of FIG. 2.

To implant the catheter into the urethra, the catheter is first inserted in the urethra with the fins closed. Then the push-tube is pushed into the catheter until it mates with the catheter body (i.e., element 3a mates with element 4b) and locks into position. Applying a force which deforms the catheter body enough so that elements 3a and 4b separate and the push-tube is no longer locked in position, allows the fins to close and consequently allows for removal of the catheter from the body.

Figure 3B:
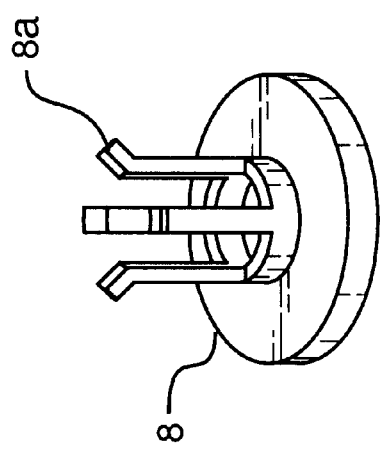
FIG. 3 is a perspective view of a pusher and grabber mechanism used to aid in the insertion of the urethral catheter.
Figure 3A:
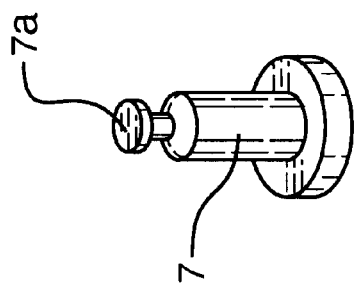
Figure 4B:
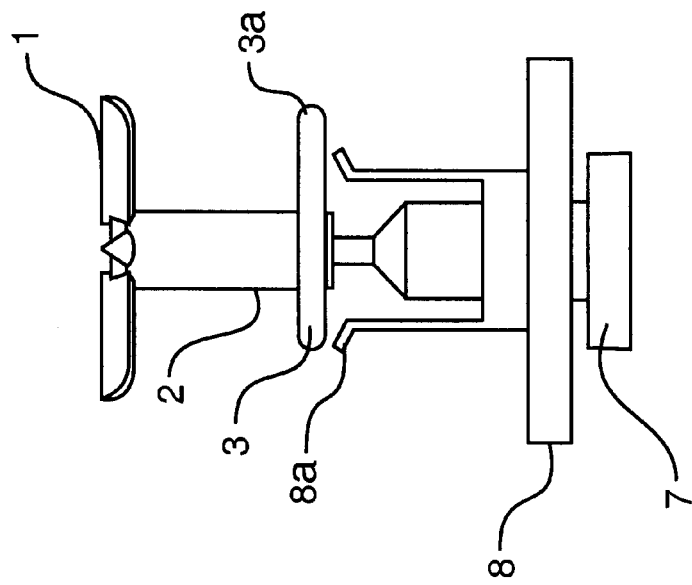
FIGS. 4a and 4b are side plan views showing the pusher and grabber in use with the urethral catheter or plug; and, FIG. 5 is a cross-sectional view of a catheter and push-tube in the closed and open positions, adapted for use in a male urethra.
Figure 4A:
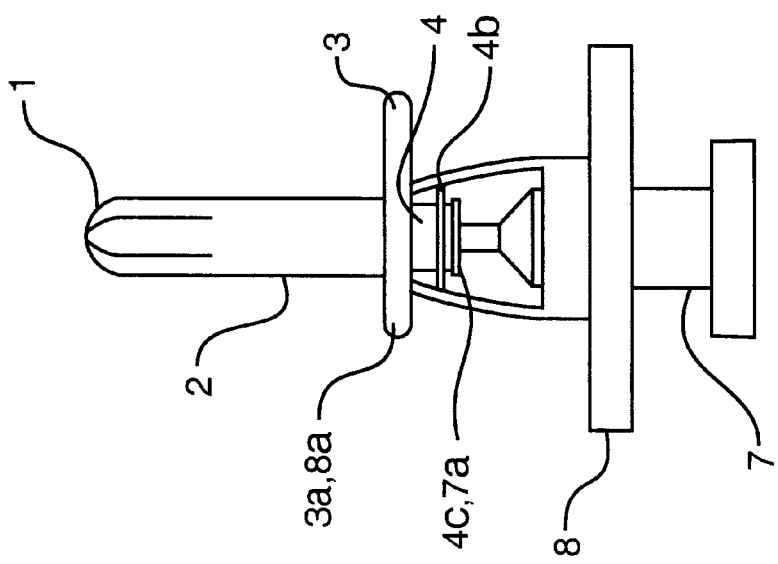

FIG. 3 shows two elements which can be used in aid in the insertion of the catheter in the body. Element 7, the injector, is used to help push the push-tube into the catheter for opening the fins. Element 8, the grabber, is used to hold the catheter body while the push-tube is pushed. FIG. 4 shows the injector and grabber in use. The grabber has outwardly angled tips (8a) which can fit into the slot 3a of the catheter. After the grabber and catheter are assembled in this manner, the push-tube is partially inserted into the catheter body as shown in FIG. 4a. The pusher-tip (7a) of the injector 7 is then aligned with the end of the push-tube (4c). After positioning the catheter within the body, the user would grab the injector 7 and grabber 8 as he would a syringe; thumb on the pusher and two fingers on the grabber. Pulling the grabber 8 towards the pusher of the injector 7 spreads the tips 8a and deforms the slot 3a in the catheter so that it can mate with surface 4b on the push-tube. After the push-tube is fully inserted and mated with the catheter, continued pulling of the grabber frees its tips 8a from the catheter (see open configuration in FIG. 4b). At this point the catheter is fully inserted in the body, the fins are open, and the grabber and the pusher can be removed. To remove the catheter from the body, the user must only deform the external tabs (element 3 on the catheter) by bending or stretching so that the push-tube pops out. Once this happens, the catheter can be freely removed since the fins return to the closed position by their inherent elasticity and resiliency.

The basis of this invention is that the fins flare open because a force is applied to the center of the fin base by a push-tube while the outer edge of the fin base is held by the catheter body. In another embodiment of this invention, the outer edge of the flare base is held by a string or wire. In this embodiment, a grabber would not be necessary to hold the catheter body. Instead, the string would be pulled while the push-tube is pushed. The string would then be tied in place to lock the fins in the flared open position. Releasing the string would allow the flares to close and allow for the removal of the catheter.

The specific shape of the tube and/or the fin can take many forms. Likewise, the mating portions between the tube and the catheter can take many forms which will all likewise hold the push-tube in place, as desired.

Figure 5A:
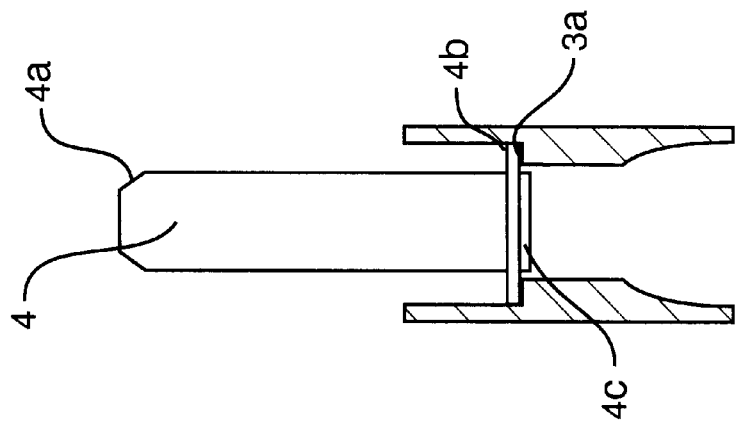
Figure 5B:
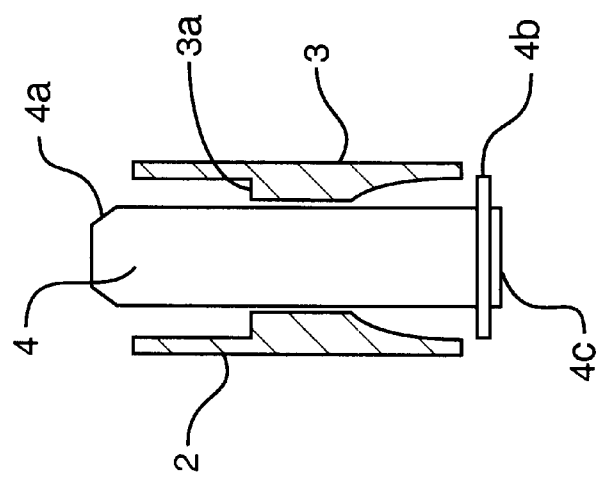

FIG. 5 shows another embodiment of the mating between the push-tube and catheter. This embodiment is appropriate for use on a catheter to be used in the male urethra. The outer diameter of the mating section is the same as the catheter body diameter. Consequently, the mating area can be located within the urethra. The insertion of this catheter within the male urethra would be accomplished using a pusher and grabber with distal portions that fit within the urethra. The proximal portion of the pusher and grabber would remain external to the body for remote opening of the fins within the bladder. After deforming so that the push-tube and the catheter body are mated and locked in position, the pusher and grabber can be removed.

In another embodiment of this invention the mated catheter and push-tube have the same outer diameter as the catheter body. In another embodiment, the deformation necessary to mate the catheter to the push-tube locally enlarges the catheter diameter. If this enlarged section is located in the prostatic urethra it can serve the purpose of preventing the sliding of the catheter further into the bladder.

Removal of the catheter from the urethra would be accomplished by inserting into the urethra a mechanical device which would deform the catheter enough to release the push-tube. The mechanical device may take the form of a balloon or any other device which can stretch the catheter enough to release the push-tube.

The detailed description of the device is not limited to use in the urethra but is applicable to any kind of tube, catheter or plug used in the body with a fixation mechanism. One example of such a tube is a ureteral catheter in which the fins will hold the catheter in the kidney pelvis (instead of a pig-tail ureteral catheter). Another embodiment is a gastric or jejunal feeding tube as well as peritoneal and post-operative feeding tubes. The system may also be applied for closing holes in the body such as in arterial or vein post-puncture bleeding, heart atrio-ventricular septal defects, or atrio-ventricular or intestinal fistulas and punctures.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the amended claims.

I claim:

1. A method for use of a catheter in the human body, comprising the steps of:

(a) inserting a tube into the human body in which said tube is used for fixation of a pump, said tube having a distal end and a proximal end, said distal end comprising one or more fins, said fins having an open position defining a large diameter and a closed position of relative small diameter and being maintained in said open and a closed position of relative small diameter and being maintained in said open position while said tube is located within a cavity of the human body; and, (b) manipulating said fins from said open position to said closed position before pulling said catheter out of its location in a cavity of the human body.

2. A method for use of a catheter in the human body, comprising the steps of:

(a) inserting a tube into the human body in which said tube is used for fixation of a pump and in which said pump is inserted into a portion of the circulatory or urinary system, said tube having a distal end and a proximal end, said distal end comprising one or more fins, said fins having an open position defining a large diameter and a closed position of relative small diameter and being maintained in said open position while said tube is located within a cavity of the human body; and, (b) manipulating said fins from said open position to said closed position before pulling said catheter out of its location in a cavity of the human body.

3. A method for use of a catheter in the human body, comprising the steps of:

(a) inserting a tube into the human body in which said tube is used to treat heart septal defects, said tube having a distal end and a proximal end, said distal end comprising one or more fins, said fins having an open position defining a large diameter and a closed position of relative small diameter and being maintained in said open position while said tube is located within a cavity of the human body; and, (b) manipulating said fins from said open position to said closed position before pulling said catheter out of its location in a cavity of the human body.

* * * * *